US011944501B2

United States Patent
Aase et al.

(10) Patent No.: US 11,944,501 B2
(45) Date of Patent: Apr. 2, 2024

(54) SYSTEMS AND METHODS FOR AUTOMATIC MEASUREMENTS OF MEDICAL IMAGES

(71) Applicant: GE Precision Healthcare LLC, Wauwatosa, WI (US)

(72) Inventors: Svein Arne Aase, Trondheim (NO); Siying Wang, Wuxi (CN); Sten Roar Snare, Horten (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 7 days.

(21) Appl. No.: 17/651,389

(22) Filed: Feb. 16, 2022

(65) Prior Publication Data

US 2023/0255602 A1     Aug. 17, 2023

(51) Int. Cl.
A61B 8/08     (2006.01)
A61B 8/00     (2006.01)
A61B 8/02     (2006.01)
G16H 30/20    (2018.01)

(52) U.S. Cl.
CPC .............. *A61B 8/5223* (2013.01); *A61B 8/02* (2013.01); *A61B 8/463* (2013.01); *A61B 8/465* (2013.01); *A61B 8/467* (2013.01); *A61B 8/485* (2013.01); *A61B 8/488* (2013.01); *A61B 8/5207* (2013.01); *G16H 30/20* (2018.01)

(58) Field of Classification Search
CPC ......... A61B 8/5223; A61B 8/02; A61B 8/463; A61B 8/465; A61B 8/467; A61B 8/485; A61B 8/488; A61B 8/5207; G16H 30/20
See application file for complete search history.

(56) References Cited

U.S. PATENT DOCUMENTS

| | | | |
|---|---|---|---|
| 7,995,820 B2 * | 8/2011 | de Barros Carneiro | G06V 10/446 600/443 |
| 11,540,808 B2 * | 1/2023 | Nouri | A61B 8/52 |
| 11,620,740 B2 * | 4/2023 | Rothberg | G06T 7/0002 382/128 |
| 11,717,183 B2 * | 8/2023 | Zou | G06T 7/60 600/443 |
| 2021/0369241 A1 | 12/2021 | Aase | |

* cited by examiner

*Primary Examiner* — Eliza A Lam
(74) *Attorney, Agent, or Firm* — McCoy Russell LLP

(57) ABSTRACT

Methods and systems are provided for performing automated measurements on medical images. In one example, a method includes acquiring a first ultrasound image and a second ultrasound image in accordance with a patient exam workflow, wherein the patient exam workflow calls for one or more measurements including a first measurement to be obtained on at least the first ultrasound image, automatically assessing whether the first ultrasound image is suitable for obtaining the first measurement during a time period where the second ultrasound image is being acquired, and if the first ultrasound image is automatically assessed as being unsuitable for obtaining the first measurement, automatically prompting the user, while the second ultrasound image is still being acquired, to reacquire the first ultrasound image.

8 Claims, 7 Drawing Sheets

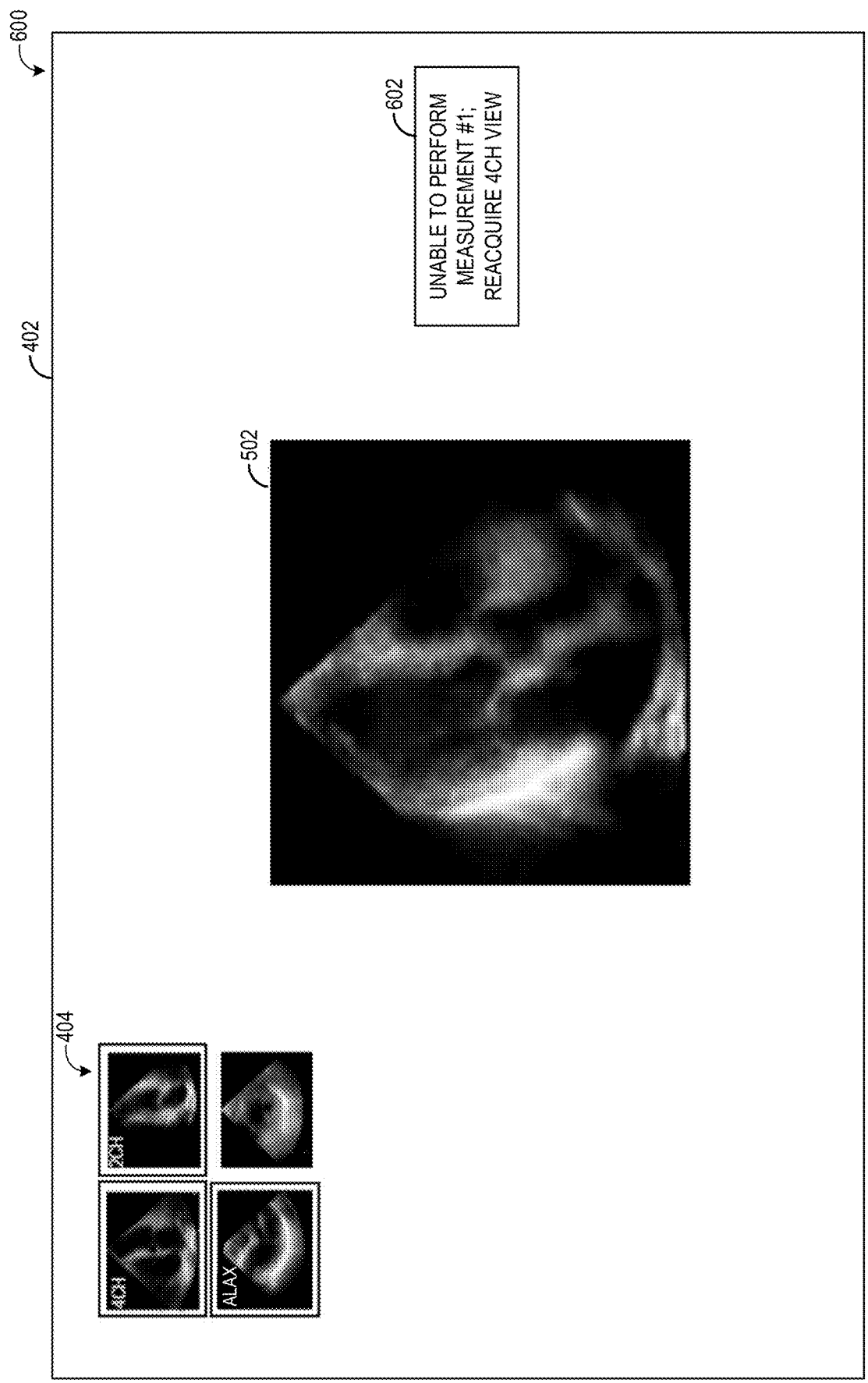

SYSTEMS AND METHODS FOR AUTOMATIC MEASUREMENTS OF MEDICAL IMAGES

TECHNICAL FIELD

Embodiments of the subject matter disclosed herein relate to ultrasound imaging, and more particularly, to the performance of automatic measurement procedures.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method includes acquiring a first ultrasound image and a second ultrasound image in accordance with a patient exam workflow, wherein the patient exam workflow calls for one or more measurements including a first measurement to be obtained on at least the first ultrasound image, automatically assessing whether the first ultrasound image is suitable for obtaining the first measurement during a time period where the second ultrasound image is being acquired, and if the first ultrasound image is automatically assessed as being unsuitable for obtaining the first measurement, automatically prompting the user, while the second ultrasound image is still being acquired, to reacquire the first ultrasound image.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 6 shows a third view of the example user interface during the automated measurement process.

DETAILED DESCRIPTION

Figure 1:
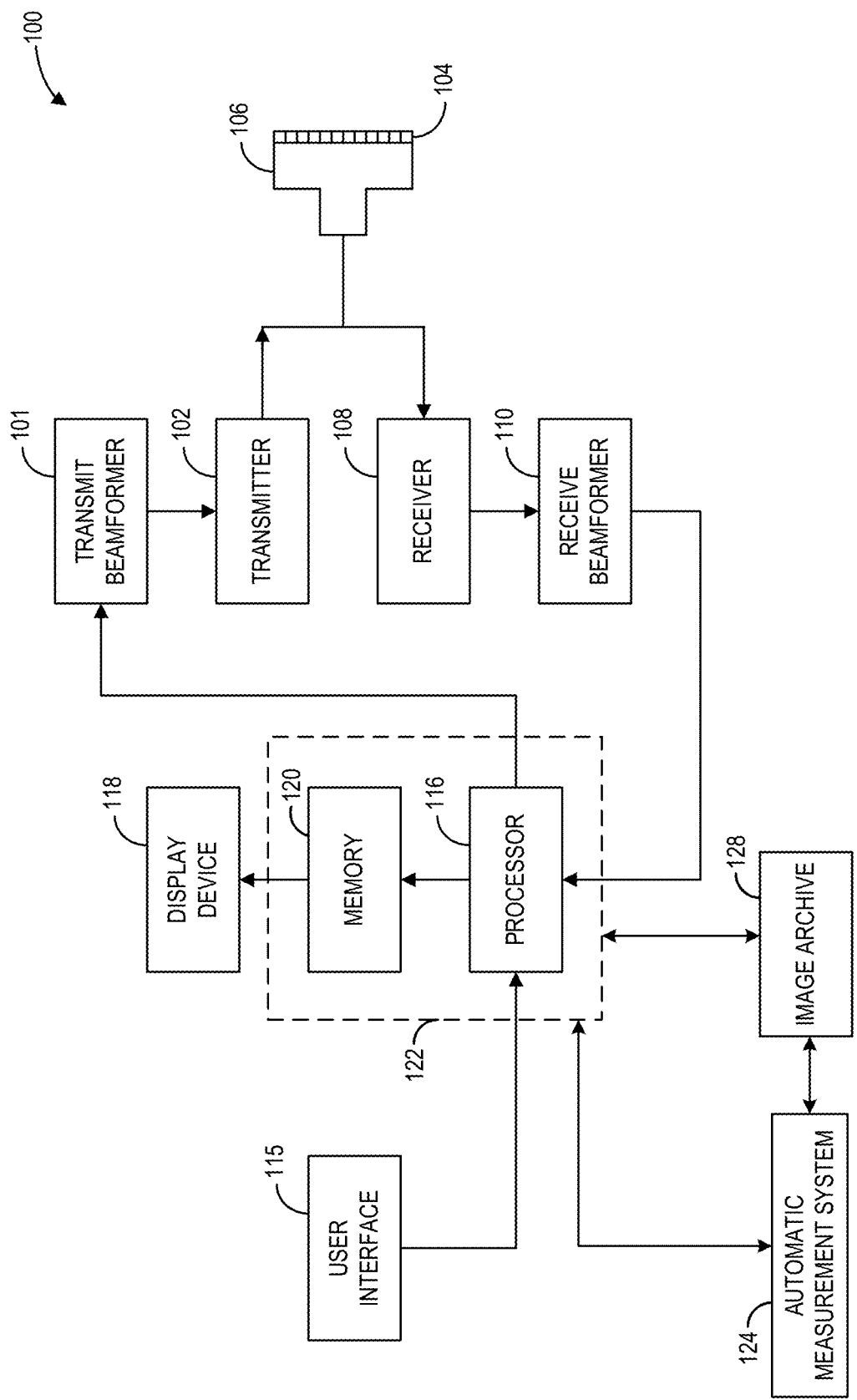
FIG. 1 shows a block diagram of an embodiment of an ultrasound system.

Ultrasound is commonly used as a non-invasive, non-radiological technique to acquire internal images of patients. Ultrasound images may be analyzed to diagnose or rule out patient conditions, such as tumors, heart defects, and the like. Some patient exam workflows that may be carried out for diagnosing a patient condition may include one or more measurements of anatomical features in one or more ultrasound images. For example, echocardiograms (also referred to herein as echoes) may include the acquisition and analysis of a plurality of ultrasound images of the heart, where a plurality of measurements may be performed on the ultrasound images to evaluate the condition of the heart, such as a thickness of the interventricular septum (IVS), ejection fraction, strain, and the like. To increase consistency in the measurements across different clinicians and expedite the time each patient exam takes, some of the measurements may be performed automatically by a computing device configured to receive the ultrasound images. However, the automated measurements may sometimes take several seconds to complete, e.g. on the order of ten seconds or more. Computationally expensive processing algorithms may be employed to perform the measurements, which the user may view in order to approve a result of the measurement only once the algorithms are complete. Furthermore, these measurements may be performed on a computing device with relatively few available resources (e.g. processing power and memory). Traditionally, the automatic measurements are initiated manually by an operator. Initiating the automatic measurement manually and waiting for its completion requires user time, and may lead to frustration and increased delays when several measurements are required.

Thus, according to embodiments disclosed herein, one or more automatic ultrasound measurements may be performed on ultrasound images acquired as part of a patient exam in the background while active imaging is still ongoing, such that measurements are performed automatically without user input. The automatic measurements may be performed while the scanner (e.g., ultrasound imaging system) is being utilized to obtain the ultrasound images as part of the patient exam, for example the performance of the automatic measurements may be triggered by a determination that each ultrasound image dictated by the automatic measurement has been obtained (e.g., the proper anatomical features, in the proper planes, have been acquired). The processing algorithms for performing the automatic measurements may thus be performed in the background while active ultrasound imaging is still ongoing and then made available to the user through the use of a notification that may be displayed on the user interface via which the user may be viewing the ultrasound images acquired as part of the patient exam workflow.

The automatic measurements may be performed with the most currently available data from the ultrasound system and the user/ultrasound operator may be notified whenever measurements are available. The ultrasound operator may then check the available readings quickly, since the processing will have been performed. The operator may thus be able to quickly assess the measurements, without waiting for additional processing to be performed. In some cases, the available ultrasound data may not currently be sufficient for the performance of certain automatic measurements. In such a case, the system disclosed herein may notify the operator that sufficient data is not available, prompting the user to perform some other action such as, for example, moving the ultrasound probe to a different location or holding the ultrasound probe in the same place for longer.

Figure 2:
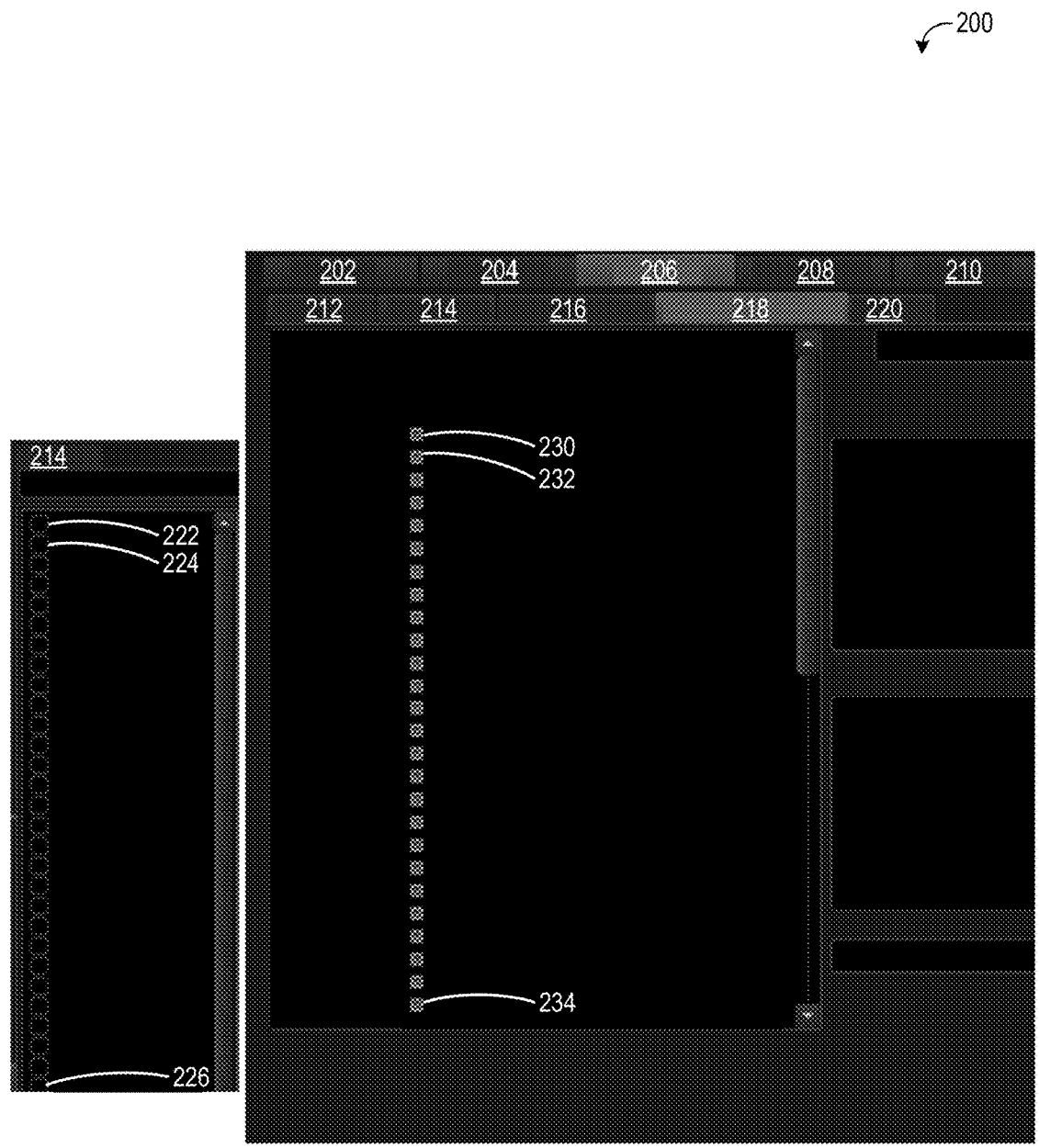
FIG. 2 shows a diagram an example embodiment of a user interface.
Figure 3A:
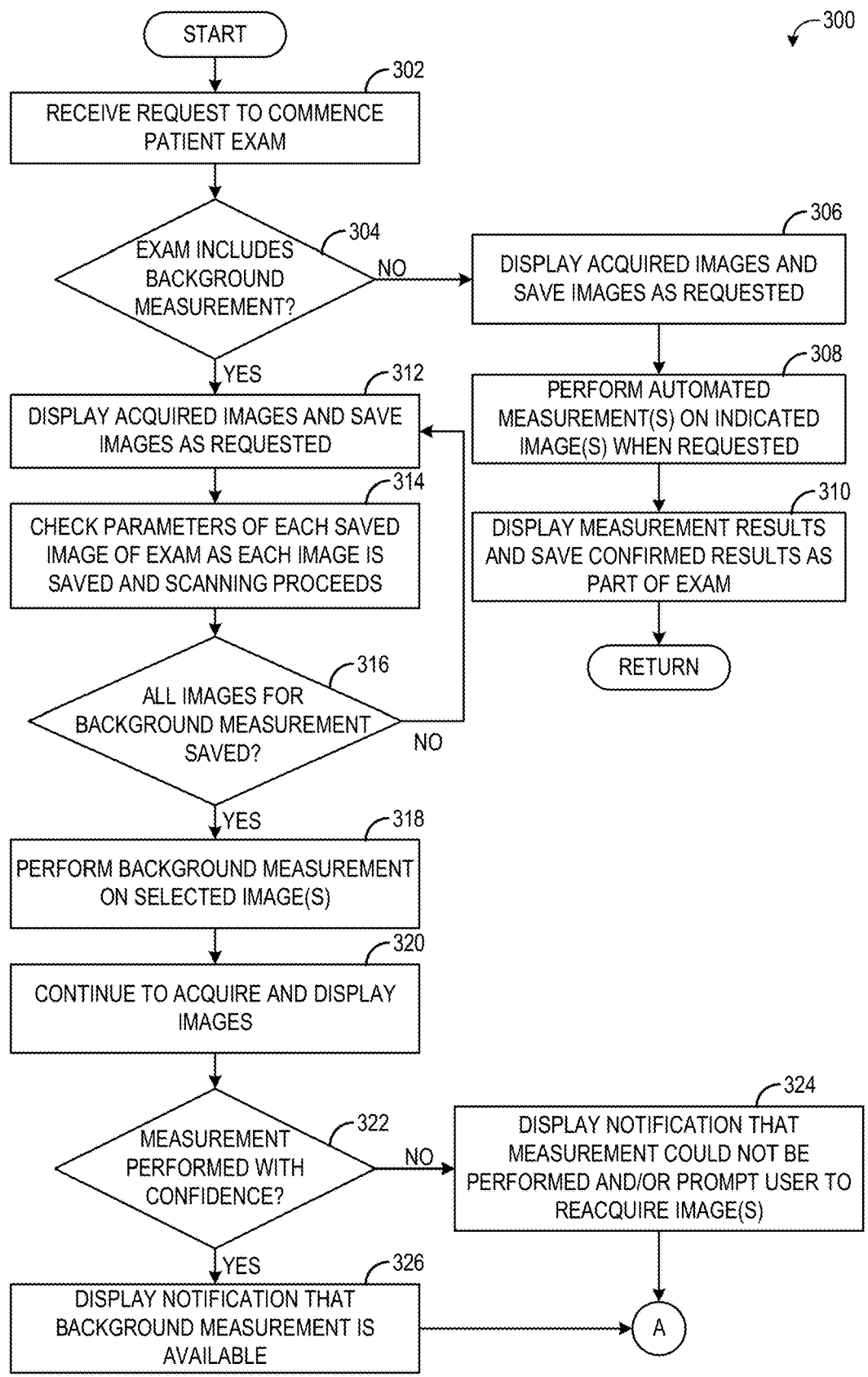
FIGS. 3A and 3B show a flow chart illustrating a method for performing automated measurements on ultrasound images obtained with an ultrasound system.
Figure 3B:
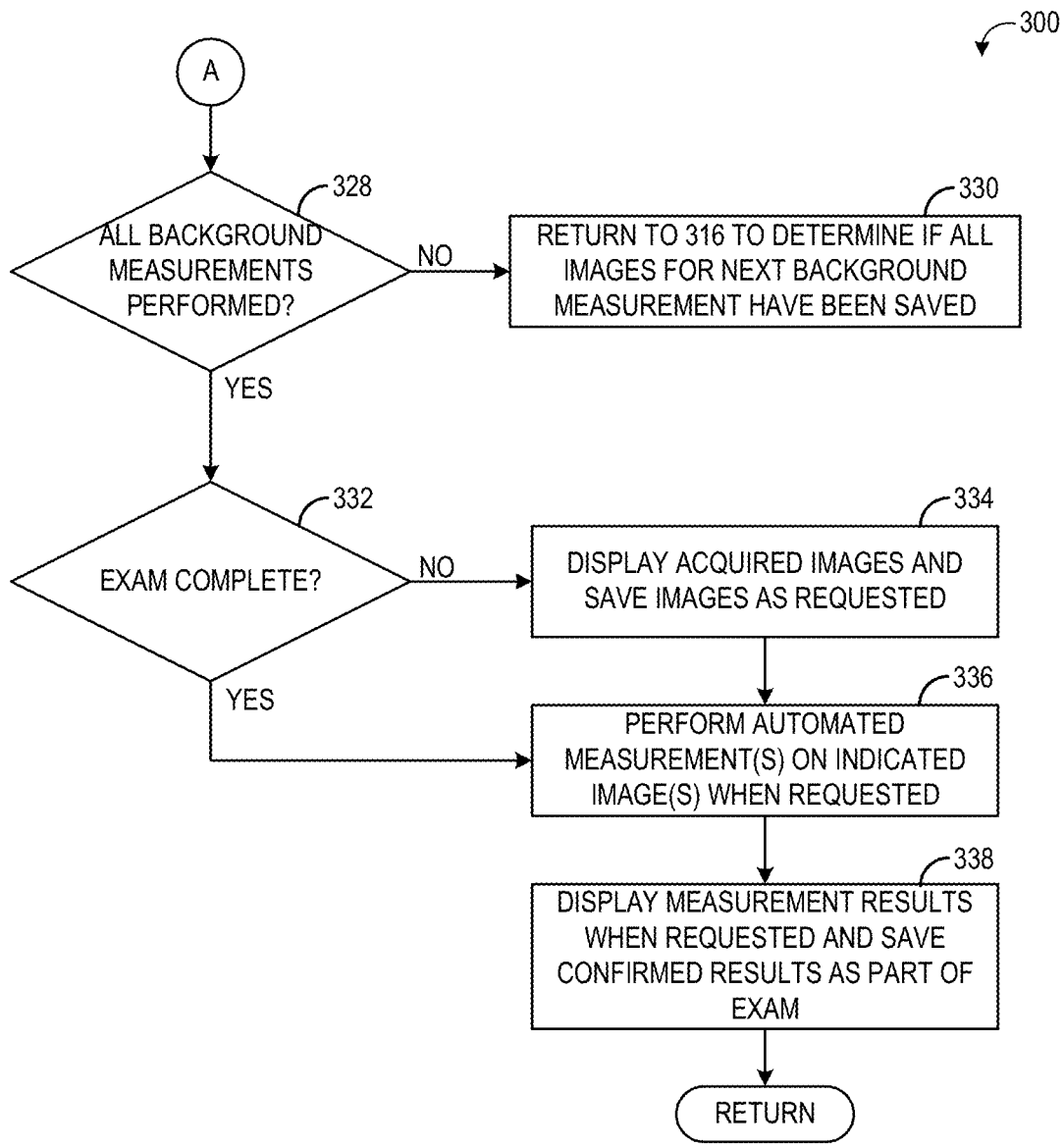
Figure 4:
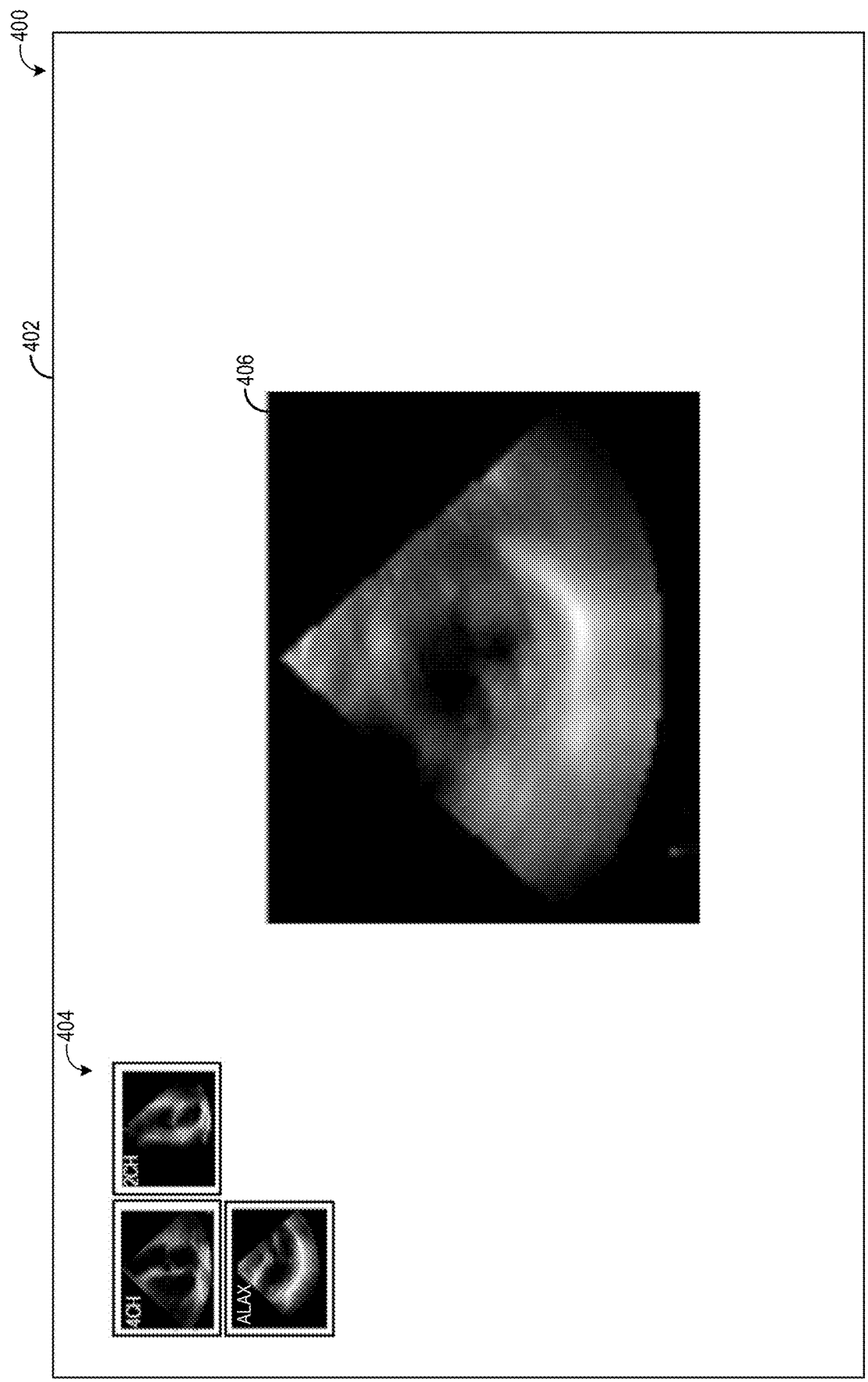
FIG. 4 shows a first view of an example user interface during an automated measurement process.
Figure 5:
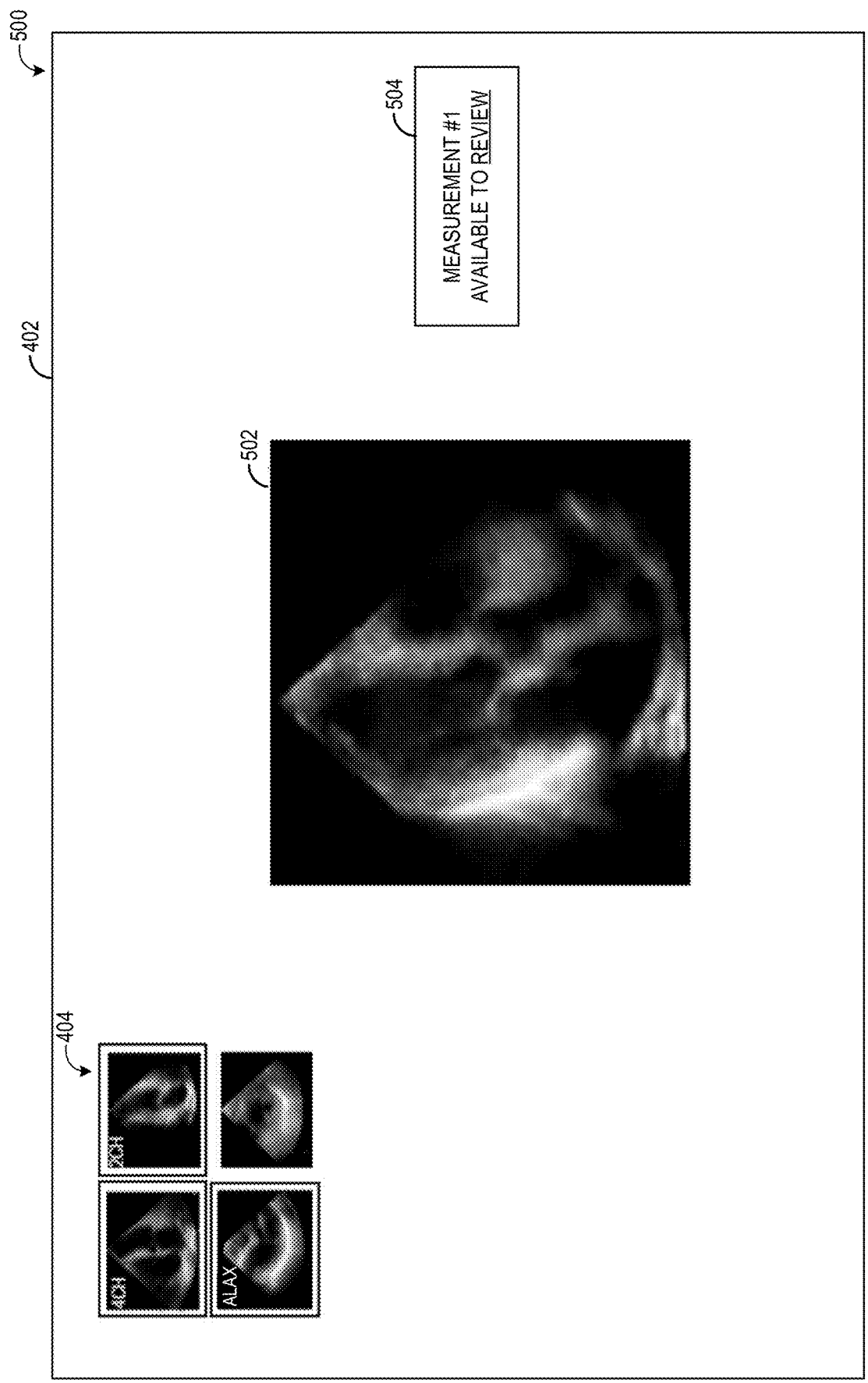
FIG. 5 shows a second view of the example user interface during the automated measurement process.

An example ultrasound system including an ultrasound probe, a display device, and an imaging processing system are shown in FIG. 1. Via the ultrasound probe, ultrasound images may be acquired and displayed on the display device. An interface displayed on a display device of FIG. 1 is shown in FIG. 2. Via the interface, an ultrasound operator may view ultrasound images as the images are acquired, select acquired ultrasound images to be saved as part of a patient exam workflow, and perform and/or view measurements of anatomical features in the ultrasound images, which may include viewing measurements performed automatically in the background during active imaging, as illustrated by the method of FIGS. 3A and 3B. Example interface views that may be displayed during the execution of the method of FIGS. 3A and 3B are shown in FIGS. 4-6.

The background measurements disclosed herein may be performed using medical images in order to measure anatomical features in order to confirm or rule out patient conditions or monitor an ongoing patient condition, for example. An example ultrasound imaging system usable to generate medical images that can be used to perform the background measurements as disclosed herein is shown in FIG. 1. However, it is to be appreciated that an ultrasound imaging system is presented herein as an example medical imaging system and that the background measurements may be performed with other medical images that may be obtained and displayed in real-time or near real-time without departing from the scope of this disclosure, such as x-ray/fluoroscopy images, optical coherence tomography images, visible light images, and the like.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic wave. In this way, transducer elements 104 may convert electronic transmit signals into acoustic transmit beams.

After the elements 104 of the probe 106 emit pulsed ultrasonic signals into a body (of a patient), the pulsed ultrasonic signals reflect from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data.

The echo signals produced by transmit operation reflect from structures located at successive ranges along the transmitted ultrasonic beam. The echo signals are sensed separately by each transducer element and a sample of the echo signal magnitude at a particular point in time represents the amount of reflection occurring at a specific range. Due to the differences in the propagation paths between a reflecting point P and each element, however, these echo signals are not detected simultaneously. Receiver 108 amplifies the separate echo signals, imparts a calculated receive time delay to each, and sums them to provide a single echo signal which approximately indicates the total ultrasonic energy reflected from point P located at range R along the ultrasonic beam oriented at angle θ.

The time delay of each receive channel continuously changes during reception of the echo to provide dynamic focusing of the received beam at the range R from which the echo signal is assumed to emanate based on an assumed sound speed for the medium.

Under direction of processor 116, the receiver 108 provides time delays during the scan such that steering of receiver 108 tracks the direction θ of the beam steered by the transmitter and samples the echo signals at a succession of ranges R so as to provide the proper time delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the real RF data and generates complex data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

The processor 116 and memory 120 may be included in a computing device 122. Computing device 122 may be a local device configured to be positioned in the same room/area as the probe 106 and may be coupled to the probe 106 via a wired or wireless connection. The computing device 122 may include a communication subsystem that may allow computing device 122 to communicate with additional external computing devices. As shown, computing device 122 is communicatively coupled to an automatic measurement system 124 and an image archive 128. Automatic measurement system 124 may be a computing device having resources (e.g., memory, processors) allocated to performing automated measurements on ultrasound images. As will be explained in more detail below, the automatic measurement system 124 may automatically perform measurements on ultrasound images of a patient. Some measurements performed by the automatic measurement system 124 may be performed in the background while images of the patient are still being obtained by the ultrasound system, with little to no input from the user. The automatic measurement system 124 may notify the ultrasound operator of the availability of measurements once the automatic measurements have been completed. The results of the measurements may be displayed, for example on display device 118, at the operator's request. The automatic measurement system 124 may perform the automatic measurements using images from obtained using the probe 106, which may be saved (and accessed by the automatic measurement system 124) in memory, such as in memory 120 and/or in an image archive 128. Image archive 128 may be a picture archiving and communication system (PACS), a vendor neutral archive (VNA), or another suitable storage system configured to store patient exams (including ultrasound images). While not shown in FIG. 1, information stored on image archive 128 may be accessible through a separate computing device, referred to as a workstation, that may have a display device, user input devices, etc.

During a patient exam workflow where ultrasound images of a patient are acquired, the automatic measurement system 124 may perform a variety of tasks in order to generate the automatic measurements. This may include obtaining images from the computing device 122 and/or image archive 128, performing one or more processing algorithms (e.g., identifying the scan plane of each saved image, segmenting one or more anatomical features in one or more ultrasound images, measuring features within and/or across one or more ultrasound images), and generating output displayable on display device 118 (e.g., notifications, measurement results). At least some of the tasks may be initiated without operator intervention, and may be triggered by certain conditions, such as particular anatomical features being visible in the ultrasound images. The availability of automatically-generated results may be indicated on the display 118.

While FIG. 1 shows the ultrasound computing device (e.g., computing device 122), the automatic measurement system 124, and image archive 128 as separate devices, it is to be understood that in some examples, one or more of the devices may be combined in a single device. For example, the automatic measurement system 124 may reside on the image archive 128. In still further examples, some or all aspects of automatic measurement system 124 may be included on computing device 122.

Turning now to FIG. 2, it shows an embodiment of an interface 200 that may be displayed with the system of FIG. 1. In one example, the interface 200 may be displayed on a display device such as display device 118 of FIG. 1, or on a separate display device communicatively coupled to a storage device configured to save medical images, such as a PACS workstation. Interface 200 may display ultrasound images, measurements of features within the ultrasound images, a plurality of diagnosis codes, findings, and/or tags, user interface control buttons, etc., to a user, allowing the user (e.g., a clinician) to select ultrasound images to be saved as part of a patient exam, perform measurements and/or view measurement results, and apply diagnosis codes, findings, and/or tags to be included as part of the current patient exam. As used herein, a patient exam may include one or more medical images of a patient, such as one or more ultrasound images, and associated diagnosis codes, findings, tags, and/or measurements that are selected, performed, or otherwise applied by a clinician. To complete the patient exam, the clinician may analyze the one or more medical images, perform measurements of anatomical features present within the one or more medical images, and use the interface 200 to approve measurements and associate diagnosis codes, findings, and/or tags with the one or more medical images, which may all be saved as part of the patient exam. The interface 200 may include elements designed to notify the operator of automatic measurements being performed, automatic measurements already completed, and/or automatic measurements unable to be completed due to insufficient data. A patient exam may also be referred to herein as a patient report. Further, the process of acquiring ultrasound images, performing measurements on the acquired ultrasound images, and optionally associating diagnosis codes may be referred to as a patient exam workflow, where the patient exam workflow may include standard image planes and/or measurements that are to be acquired and performed to diagnose or rule out one or more given patient conditions.

Menu buttons, such as first menu button 202, second menu button 204, third menu button 206, fourth menu button 208, and fifth menu button 210, may represent selectable menus the user may choose when interacting with the system, labeled accordingly. A selected menu may be visually indicated by a color change, such as third menu button 206. In one example, third menu button 206 may be a menu for reports, where the user may view additional menus/submenus in order to select diagnosis codes, findings, etc., to be included in the report.

Submenu buttons, such as first submenu button 212, second submenu button 214, third submenu button 216, fourth submenu button 218, and fifth submenu button 220, may represent selectable submenus the user may choose when interacting with a selected menu of the system, labeled accordingly. A selected submenu may be visually indicated by a color change, such as fourth submenu button 218.

In one example, second submenu button 214 may be a submenu for automatic measurement notifications, where a list of available measurements may be displayed when the second submenu button 214 is selected. All available measurements, including a first available measurement 222, a second available measurement 224, and an Nth available measurement 226 may be displayed, where N may be a number of total available measurements in the available measurements submenu. If the user selects one of the available measurements, the results may be displayed to the user. If the automatic measurements cannot be performed, a notification may be displayed, for example, in the area corresponding to the first available measurement 222. In some examples, a user may select an automatic measurement from measurements submenu and the selection may trigger initiation of the automatic measurement. The diagnosis codes may include diseases, disorders, symptoms, or other clinically-relevant observations, and in some examples may be defined by national or international regulatory/governing bodies, such as ICD codes. In some examples, the user may specify the type of exam being conducted (e.g., an echocardiogram) via the interface 200, and a subset of automatic measurements and/or possible diagnosis codes related to the exam type may be displayed.

In one example, fourth submenu button 218 may be a submenu for automatic measurement results, where a list of results may be displayed upon the fourth submenu button 218 being selected, allowing the user to look through the results of the automatic measurements. All results, including a first result 230, a second result 232, and an Mth result 234 may be displayed, where M may be a number of total results in the findings submenu. Results may be generated from one or more automatic measurements, which may be generated in the background during ultrasound scanning. The results may be calculated based on the latest data available from the ultrasound system, for example, the images saved in memory 120 and/or image archive 128. Calculations utilized in the processing of the measurement results may be performed in the background, without user intervention.

Thus, interface 200 may be displayed during a patient exam workflow where medical images may be obtained and reviewed by one or more clinicians such as a sonographer and/or a cardiologist to confirm or rule out one or more patient conditions based on the results of the automatic measurements. In order to review the automatic measurements, the clinician may view the data obtained automatically by the automatic measurement system. In the case that an automatic measurement is generated with low confidence or cannot be generated, a notification may be output via the interface 200, which may prompt the ultrasound operator or clinician to reacquire one or more ultrasound images (e.g., due to the initial image being low quality) or acquire an image needed for the automatic measurement that has yet to be acquired. If a new image is obtained, the automatic measurement (and its associated processing) may be performed again. It may be repeated, for example, by the automatic measurement system 124, which may perform calculations in the background while scanning is occurring. Automatic measurements and associated processing steps may be initiated automatically by the automatic measurement system using, for example, anatomical data.

FIG. 3A and FIG. 3B show a method 300 for performing automatic measurements during a patient exam. Method 300 may be implemented with the components of the ultrasound system of FIG. 1 and may be carried out according to instructions stored in non-transitory memory of a computing device, such as computing device 122 and/or automatic measurement system 124.

Method 300 includes, at 302, receiving a request to commence a patient exam. The request may include user selection of a patient exam type, such as an echo, from a list of available patient exam types displayed on a user interface, such as interface 200. The selected patient exam may have a workflow that dictates which anatomy views/scan planes (each showing selected anatomical features in a preferred view plane) are to be obtained as part of the patient exam. The workflow may further dictate (or include as options) which measurements are to be performed on the obtained images as part of the patient exam.

At 304, method 300 determines if the selected patient exam includes one or more background measurements that are to be performed as part of the patient exam workflow. The one or more background measurements may include measurements that are to be performed on selected ultrasound images while the patient exam workflow is ongoing and ultrasound images of the patient are still being acquired. The background measurements may be performed by the computing device (e.g., automatic measurement system) automatically and without specific user input commanding the measurements be performed. The determination of whether or not the patient exam includes one or more background measurements may be based on user- or administration-specified configuration settings for the patient exam type. For example, an operator of the ultrasound system may indicate via a configuration file saved on the computing device that one or more background measurements should be performed each time the selected patient exam type is performed, and these settings may be saved and applied when each patient exam of the selected type is performed. The settings may apply to all future same exam types without further user input other than actuation of the ultrasound probe. In this way, the user may not provide any input with regard to automatic background measurements being executed other than a one-time modification of the settings. As a specific example, the operator may adjust or confirm settings via the configuration file to indicate that each time that operator performs an echo, one background measurement is to be performed (e.g., myocardial wall strain measurements, which may be obtained via a process referred to as Automated Functional Imaging) and the settings may be saved and applied for all future echoes performed by that operator. In some examples, the one or more background measurements may be set by an administrator (such that all echoes performed at a given healthcare facility include the one or more background measurements) or the one or more background measurements may be set during manufacture.

At 304, if the exam does not include a background measurement, method 300 proceeds to 306, where method 300 includes displaying acquired images and saving images as requested, e.g. through the use of a manual control on the ultrasound console. For example, the operator may control an ultrasound probe (such as probe 106) to acquire ultrasound data that is processed into ultrasound images (e.g., by the computing device 122) as part of the patient exam workflow, and the ultrasound images are displayed on the interface in real-time as the images are acquired (e.g., at a frame rate of 10-30 Hz or higher). The operator may select ultrasound images (or ultrasound cine loops, which may be a series of sequential images obtained over time) to save either temporarily or permanently as part of the patient exam via selection of a freeze and/or save button on the ultrasound probe, a console of the ultrasound system, or on a touch screen/user interface (images that are not saved by the operator may be temporarily stored in a first-in first-out buffer and thus eventually be automatically deleted). At 308, method 300 includes performing one or more automated measurements on one or more indicated images when requested. These automatic measurements may be manually-initiated (and thus are not background measurements), and may include measurements of selected anatomical features, such as area, velocity, thickness, blood flow, tissue tracking, ejection fraction, strain, etc. At least some of the measurements may be performed with a low computational intensity compared to the background measurements. The indicated images may be selected by the user and/or selected automatically in response to a user request to initiate the one or more automatic measurements.

At 310, method 300 includes displaying measurement results and saving confirmed results as part of the patient exam. Measurement results may be displayed via the interface (such as interface 200) and may include values for the selected measurements (e.g., a value indicating an area of a selected anatomical feature, another value indicating a thickness of a selected anatomical feature, etc.). After the measurements are presented to the user, the user may confirm whether each measurement should be saved in the patient exam, e.g., the user may indicate if one or more of the results is accurate, based on expertise. If a measurement is not deemed to be accurate, the user may decide not to confirm the results and the results may not be saved in the patient exam. Accurate measurements may be confirmed and saved as part of the patient exam. The patient exam may be saved in a suitable location, such as the image archive 128.

Returning to 304, if the patient exam includes at least one background measurement, method 300 proceeds to 312, where method 300 includes displaying acquired images and saving the acquired/displayed images as requested, which may be performed similarly to the image acquisition and storage of 306. As explained above at 306, the acquired images may be displayed at a designated area within the interface. User requests to save the acquired images may be given through, for example a button or menu which specifies that the images are to be saved. The acquired images may be sourced from the current ultrasound exam process, and the current image that is displayed on the interface continuously updates as further images are acquired. Further, each saved image may be displayed as a thumbnail on the interface, as explained in more detail below with respect to FIGS. 4-6. In some examples, a single ultrasound image (e.g., a single frame) may be saved each time the user indicates an image should be saved. In other examples, additionally or alternatively, a series of ultrasound images (e.g., multiple frames) may be saved as a cine loop, in response to selected user input. For example, if the user selects a save button, a single image may be saved. If the user selects a cine loop button, all images that are acquired while the user is selecting the cine loop button may be saved. Further, while 2D images and/or cine loops are described and illustrated herein, in some examples, 3D images and/or 3D video loops (e.g., 4D images) may be acquired and saved as part of the patient exam. Automatic measurements (including background measurements) may be likewise performed with 3D images or videos.

At 314, method 300 includes checking parameters of each saved image and/or cine loop of the exam as each image is saved and scanning proceeds. The parameters of each image and/or cine loop that may be checked include meta parameters of the acquisition performed to obtain the image or cine loop. The meta parameters may include the mode used to acquire the image or cine loop (e.g., B-mode, M-mode, Doppler, etc.), the depth of the image or the image of the cine loop, and the frame rate. Each background measurement may include specified meta parameters for the image(s) and/or cine loop(s) to be used to perform the background measurement, such as a specified mode (e.g., B-mode), a specified depth (e.g., within a range of depth value), and a specified frame rate (e.g., 35-40 frames per second). Thus, checking the meta parameters may include checking that each image or cine loop was acquired with the specified meta parameters.

The parameters that may be checked further include physiological conditions of the patient during acquisition (such as heart rate), the anatomy view of each image and/or cine loop, the image quality of each image and/or cine loop, anatomical consistency across the image(s) and/or cine loop(s) needed for the background measurement, and/or initial image analysis rationality. The anatomy views may be identified automatically via an anatomy view model, which may be a deep learning model (e.g., neural network) or another suitable machine learning-based model that is trained to identify the anatomy view (also referred to as a scan plane) of each saved image. When an image is saved, the image may be entered as input to the anatomy view model, which may output the anatomy view of the image (e.g., apical 4-chamber view, parasternal long axis view, etc.). In other examples, the anatomy view may be identified manually by the user or another qualified medical professional. The anatomy view identified at 314 may also be saved alongside the image itself. In some examples, the anatomy view may be displayed with the thumbnail image. When a cine loop is saved, one or more images of the cine loop may be entered as input to the anatomy view model to determine the anatomy view of the images within the cine loop, which may assume that the same anatomy view is imaged in each image of the cine loop.

The image quality of each image and/or cine loop may be determined based on an initial image analysis of each image and/or cine loop. For example, the background measurement may dictate that a specific anatomical structure, such as the left ventricle, be segmented in one or more of the images and/or cine loops. The initial image analysis may include segmenting the anatomical structure to identify the anatomical structure in the image(s) and/or cine loop(s), such as with a segmentation model. Thus, checking the image quality may include confirming if the segmentation model can segment the anatomical structure in each image and/or cine loop. The output from the initial image analysis (e.g., the segmented anatomical structure) may also be analyzed to check the anatomical consistency and the rationality of the initial image analysis. For example, the segmented anatomical structure across multiple different anatomy views (and thus images) needed for the background measurement may be compared to confirm that the anatomical structure is the same size in each image and/or cine loop. Further, the dimensions of the segmented anatomical structure may be compared to known or expected ranges for that anatomical structure to confirm the segmentation was accurately performed. Likewise, movement of the anatomical structure across the different anatomy views may be tracked and compared to known or expected ranges. It should be appreciated that only some of the parameters mentioned herein may be checked during the parameter check, or all of the parameters may be checked. Further, the parameter check may be performed on each image as soon as that image is saved. In other examples, the parameter check may be initiated once at least a threshold number of images/cine loops have been saved (e.g., three).

At 316, method 300 determines if all images and/or cine loops for a given background measurement have been saved. As explained above, the parameters of each image and/or cine loop are checked as each image/cine loop is saved. If a given image passes the parameter check (e.g., the given image was acquired with the specified meta parameters, with the patient in the specified physiological condition, and the initial image analysis indicates the image is of sufficient quality and displays anatomical consistency and rationality), the anatomy view for the given image may be compared to a list of anatomy views needed for each background measurement. For each type of background measurement to be performed as part of the patient exam, one or more anatomy views needed to perform the background measurement may be identified and the current anatomy views may be compared to the anatomy views needed to perform each background measurement. If all the needed anatomy views for any background measurement have not been acquired and saved, method 300 loops back to 312, where additional images may be acquired and saved.

If instead at 316 all indicated anatomy views (and thus all indicated images and/or cine loops) for performing a background measurement have been acquired and saved (and, in some examples, all images pass the parameter check described above), method 300 proceeds to 318, where method 300 includes performing the given background measurement on the selected image(s) and/or cine loop(s), e.g. the images of the anatomy views needed to perform the given background measurement. In some examples, one or more parameters of the parameters to be checked as described above may be checked while the background measurement is performed. For example, when the background measurement is a strain measurement, the strain measurement may include segmenting the left ventricle in each image/cine loop. Thus, the initial image analysis described above (e.g., segmenting the anatomical structure and checking if the anatomical structure can be segmented, that the segmented anatomical structure is accurate/rational, etc.) may be performed as part of the strain measurement instead of before the strain measurement is performed. The background measurement may take a number of seconds to perform (particularly on computer systems with limited computational resources), and thus the background measurement is initialized at 318 but the background measurement may be ready at a later time, after additional images have been acquired. When execution of the background measurement is complete, all aspects of the background measurement may be saved in memory for later retrieval, including the images/cine loops used for the measurement, segmentation of the images/cine loop, and measurement results (which may include values, plots, visualizations of measured features, etc.).

As the background measurement is performed at 318, at 320, method 300 includes continuing to acquire images and display the acquired images. One or more of the above-described actions that are part of the background measurement process may be performed during acquisition of a next image. For example, the background measurement may dictate that three images, each having a specified respective anatomy view, be saved to perform the background measurement. Two out of the three images may have previously been saved by the user and identified as such by the anatomy view model. A current ultrasound image may then be acquired and saved. The method may include automatically assessing whether the current ultrasound image is suitable for obtaining the background measurement, during a time period where a next ultrasound image is being acquired. This automatic assessment may include determining if the current ultrasound image includes the third anatomy view needed for performing the background measurement. Additionally or alternatively, the automatic assessment may include determining if the current ultrasound image is of sufficient quality for performing the background measurement. For example, the anatomy view model may determine the current ultrasound image includes the third anatomy view, but a separate assessment (e.g., the parameter check described above) may indicate that the current ultrasound image was acquired with an incorrect framerate or during a period where the patient exhibited an undesired heart rate (as the background measurement may dictate that each image or cine loop used in the background measurement be acquired with the same frame rate and with the patient's heart rate at a steady, same heart rate). If the current ultrasound image is automatically assessed as being unsuitable for obtaining the background measurement, the method may include automatically prompting the user, while the next image is still being acquired, to reacquire the current ultrasound image, as explained in more detail below. Alternatively, if the current ultrasound image is automatically assessed as being suitable for obtaining the background measurement, the method may include automatically starting the obtaining of the background measurement while the next ultrasound image is being acquired. In some examples, the next ultrasound image is acquired immediately following acquisition of the current ultrasound image without any intervening images being acquired.

Accordingly, the computing device may be simultaneously performing the background measurement and processing the received ultrasound data into images. To ensure the acquired images are displayed at the desired frame rate, the background measurement may be assigned a low processing priority compared to other processing functions carried out on the ultrasound data to generate the images (e.g., beam-forming, scan-conversion), which may be assigned a higher processing priority. The processing resources of the computing device may be allocated according to the assigned priorities. For example, the processing resources may be allocated according to the assigned priorities such that more processing resources may be used to process the ultrasound data (e.g., given the higher priority of the processing of the ultrasound data) than used to perform the background measurement, ensuring that the computing device prioritizes image acquisition and display and does not experience significant slowdowns while acquiring images. Additionally or alternatively, the processing resources may be allocated according to the assigned priorities such that the execution of the background measurement is occasionally paused to allow sufficient processing resources to be used to generate the ultrasound images. In some examples, the processing of the ultrasound data that is carried out while the background measurement is performed may include performing a scan conversion process on channel data received from the ultrasound probe to form one or more ultrasound images.

At 322, method 300 determines if the given background measurement was performed with confidence. In some examples, if the background measurement was able to be performed, such that a value (or set of values), plots, and/or visualizations are generated for the background measurement, the background measurement may be determined to have been performed with confidence. In some examples, if the result of the background measurement is determined to be rational (e.g., within an expected range of values for that measurement, which may take into account anatomical defects), the background measurement may be determined to have been performed with confidence. For example, if the background measurement includes performing a segmentation of the left ventricle (LV) as part of the process to obtain the background measurement, the determination of whether the background measurement is performed with confidence may include a determination of whether aspects of the LV determined from the LV segmentation (such as LV length, area, and/or diameters) are within anatomically plausible ranges. However, if the background measurement cannot be performed or if the result of the background measurement is not rational or plausible, the background measurement may not be determined to have been performed with confidence. In still further examples, when aspects of the parameter check are carried while the background measurement is being performed, if an aspect of the parameter check does not pass (e.g., an anatomical feature of interest cannot be segmented in one of the images or cine loops), the background measurement may be determined not to have been performed with confidence.

If the background measurement was not performed with confidence, method 300 proceeds to 324, where method 300 includes displaying a notification (e.g., on the interface) that the measurement could not be performed and/or that prompts the user to reacquire one or more images or acquire one or more images that have not been acquired. For example, if the background measurement cannot be performed because a selected anatomical feature (e.g., the left ventricle) could not be segmented in one of the saved images used to perform the background measurement, the notification may include a prompt to reacquire that image (e.g., acquire a new image that includes the same anatomy view of that image), as the original image may not be of sufficient quality to perform the segmentation. In another example, if the background measurement could not be performed because one of the saved cine loops did not include a full cardiac cycle, the notification may include a prompt to reacquire that cine loop to include a full cardiac cycle. In still further examples, the notification may include a prompt for the user to manually segment a selected image or perform another suitable function to facilitate an accurate measurement result.

If, on the other hand, the background measurement is performed with confidence at 322, method 300 includes at 326 displaying a notification that the background measurement is available. Because image acquisition of the patient exam is still ongoing, the user may wish to wait until the exam workflow is complete/all images and/or cine loops have been acquired before reviewing the measurement, and thus the notification that the background measurement is available may allow the user to decide when the background measurement result should be reviewed. The notification may include a control button/link that the user may select to view the result of the background measurement. By notifying the user that the background measurement is available, the user may assume that the image(s)/cine loop(s) needed for the background measurement have been acquired with sufficient quality, which may reduce instances of the user reacquiring images or cine loops due to uncertainty about the quality of the images/cine loops. The user may view the results of the background measurement at any point during or after the exam, e.g., by selecting the control button/link displayed as part of the notification that the background measurement is available to review.

Method 300 continues in FIG. 3B, where at 328, method 300 includes determining whether or not all background measurements have been performed, e.g., by comparing the list of background measurements specified for the patient exam type to the background measurements that have already been performed with confidence (as determined at 322). If all background measurements have not been performed, e.g., if at least one background measurement still needs to be performed, method 300 returns to 316 to determine if all images and/or cine loops for the next background measurement have been saved, as indicated at 330. It should be appreciated that the process described above may be repeated for each remaining background measurement e.g., the next background measurement may be executed once all images and/or cine loops for the next background measurement have been saved, and the user may be notified the next background measurement is available to review (if the next background measurement was performed with confidence) or the user may be notified that the next background measurement could not be performed (e.g., due to one or more images and/or cine loops being of insufficient quality for performing the background measurement).

Otherwise, if the last background measurement has been performed, at 332, method 300 determines whether or not the patient exam is complete. The patient exam may be determined to be complete if the user has entered input indicating the exam is complete (e.g., selection of a control button of the user interface indicating that all images for the exam have been acquired) or via another suitable method, such as if all needed anatomy views for the exam have been acquired. If the exam is not complete, method 300 includes at 334 displaying the acquired images and saving images as requested.

If the exam is determined to be complete at 332, method 300 includes, at 336, performing one or more automated measurements on one or more indicated images and/or cine loops when requested. For example, as explained above at 308, the automatic measurements may be manually-initiated (and thus are not background measurements), and may include measurements of selected anatomical features, such as area, velocity, thickness, blood flow, tissue tracking, ejection fraction, strain, etc. The indicated images and/or cine loops may be selected by the user and/or selected automatically in response to a user request to initiate the one or more automatic measurements. The automatic, non-background measurements may be performed only in response to a user request to perform the automatic, non-background measurements.

At 338, method 300 includes displaying measurement results when requested and saving confirmed results as part of the patient exam, as explained above at 310. Measurement results may be displayed via the interface if requested by the user and may include values for the selected measurements (which may include the background measurements and the non-background automatic measurements). For example, if the user requests to view the results of a background measurement, the results may be displayed immediately (e.g., within one second), as opposed to examples where the measurement is not performed in the background. In such cases, the measurement may instead be initiated in response to a user request, and the results may be displayed after the measurement is completed, which may take 15 seconds or longer. Further, in some examples, when the user is viewing the results of a background measurement, the user may be presented with an option to override the selection of the images and/or cine loops used to perform the background measurement (e.g., select one or more different images/cine loops for the measurement), and the measurement may be performed again with the new image(s). After the measurements are presented to the user, the user may confirm whether each measurement should be saved in the patient exam. In some examples, when the user confirms the results of a background measurement, only selected aspects of the background measurement may be saved as part of the patient exam. For example, images showing the segmentation of the left ventricle may be omitted, such that the results include values, plots, and/or other visualizations of the values and do not include visualizations of intermediate steps performed to arrive at the results. In some examples, the user may not review the results of the background measurement (or any other automatic, non-background measurements) at the time of the exam and may instead enter user input requesting the results of the background measurement be saved until the user (or another user) reviews the background measurements as part of a post-exam review. In such examples, the results of the background measurement may be saved along with the saved images and/or cine loops on the local computing device (e.g., in memory 120 and/or as part of the automatic measurement system 124) or on an image archive (e.g., image archive 128). Method 300 then returns.

In this way, method 300 includes the performance of one or more background measurements that are performed while active imaging of a patient is still occurring. While the background measurements are performed during the exam while images of the patient are still being acquired, the user may choose to review the results of the background measurement(s) at any suitable time once the results are available. For example, the user may select a control button/link on the measurement results notification to bring up the results (while still more images are being acquired and recorded for the exam), and then the user may subsequently edit and/or approve the background measurement. In other examples, the user may wait until the exam is complete (e.g., all images and/or cine loops for the exam have been acquired and saved), at which point the user may select a notification of "unapproved auto-measurements available" in order to review the results of the background measurement(s). In still further examples, the system may automatically, upon the exam being deemed to be complete, display the results of the background measurements. In a still further example, if the user does not want to approve the results of the background measurements at the imaging system (e.g., because the operator of the ultrasound system is not authorized to confirm measurement results or does not have time to confirm measurement results), the user may request that the system save the exam without the background measurements being approved/confirmed. Then whoever reviews the exam in retrospect will have to review/approve the measurements. In such an example, the user who reviews the exam at a later time may still benefit from the reduced time from requesting to view the results of the background measurement(s) until the results are displayed, given that the background measurement has already been performed during the exam.

FIGS. 4-6 show example views of a user interface that may be displayed on a display device (e.g., display device 118) during execution of method 300. FIG. 4 shows a first example view 400 of a user interface (such as interface 200) during execution of a patient exam workflow, herein an echo. The user interface is displayed on a display 402. A first portion of the display area of the display 402 is allocated for a plurality of thumbnail images 404. The thumbnail images may represent ultrasound images of a patient saved by a user/operator of the ultrasound system during execution of the patient exam workflow. In first view 400, three thumbnail images are shown, indicating that three images have been saved as part of the patient exam. Each saved image is entered as input to an anatomy view model, which outputs the anatomy view of each image. In the current example, a 4-chamber view (4CH), a 2-chamber view (2CH), and a long axis view (LA) have been saved and identified by the anatomy view model. The interface includes a second portion of display area where a current image 406 is displayed. The current image is the most recent image of the patient acquired by the ultrasound system, and is updated as each new image is acquired/generated. While single images are shown in FIG. 4, it is to be appreciated that one or more of the images may represent cine loops. For example, each of the thumbnail images of FIG. 4 may be cine loops of a cardiac cycle of a heart viewed at each of the specified scan planes/anatomy views.

The output from the anatomy view model indicates that all anatomy views for a selected background measurement have been acquired (e.g., the 4CH, 2CH, and LA views). Further, each image may have passed a parameter check to indicate that each image is suitable for performing the background measurement. In one non-limiting example, the selected background measurement may be a strain measurement, and the parameter check may include checking that the meta parameters match specified meta parameters for the background measurement (e.g., that the images are all B-mode images acquired within a specified depth range and at a specified frame rate), that the heart rate of the patient during acquisition of the images was within an expected range, that the anatomy views are correct, that the left ventricle can be identified in each image, that the left ventricle is approximately the same size within each image, that the size/shape of the left ventricle in each image is reasonable (e.g., within a given range of standard sizes/shapes), and/or that the movement of the left ventricle over time (e.g., within cine loops and/or across the images/cine loops) is reasonable (e.g., within an expected range). As such, the background measurement may begin executing in the background, while imaging of the patient is still ongoing. In some examples, the images utilized for performing the background measurement may be highlighted via a suitable visualization on the thumbnail images, as shown by the black boxes around the images in FIG. 4.

FIG. 5 shows a second example view 500 of the user interface after a period of time has elapsed since the first view was displayed. In the second view 500, an additional image has been added to the plurality of thumbnail images 404, indicating that the user saved another image. The additional image is not used in the background measurement. Because imaging is still ongoing, a new current image 502 (e.g., a next image) is displayed on the interface. Second view 500 includes a notification 504 indicating that the background measurement (e.g., performed with the three images identified as explained above with respect to FIG. 4) is available to review. The notification may include a link (e.g., review being underlined) that can be selected so that the results of the measurement are displayed on the interface. By displaying the notification that the background measurement is available to review, the user/operator may reasonably assume that the measurement was able to be performed and proceed with the remaining exam and/or end the exam when desired, without having to perform any independent or otherwise time-consuming checks to ensure the correct images for performing the background measurement were obtained.

FIG. 6 shows a third example view 600 of the user interface after a period of time has elapsed since the first view was displayed. The third view 600 may be an alternative example of second view 500. In the third view 600, similar to the second view 500, an additional image has been added to the plurality of thumbnail images 404, indicating that the user saved another image. The additional image is not used in the background measurement. Because imaging is still ongoing, the new current image 502 is displayed on the interface. Third view 600 includes a notification 602 indicating that the background measurement (e.g., performed with the three images identified as explained above with respect to FIG. 4) could not be performed. The notification may include a prompt to the user to reacquire one of the images, herein the 4CH view image, due to the 4CH view image being of low quality, for example.

In this way, one or more automatic measurements may be performed in the background while active imaging is still being performed. By performing the automatic measurements in the background while active imaging is ongoing, the delay between the user requests to review the results of the measurement and when the results are presented to the user may be reduced or virtually eliminated. Further, sufficient time may be available for performing the background measurement (e.g., before a user requests to view the results of the measurement) to allow for more complex algorithms to be applied to generate the results of the measurement. The more complex algorithms/additional time available for processing may allow for more accurate measurements or for the application of measurements that may not have been previously supported.

The technical effect of performing an automatic measurement on one or more ultrasound images and/or cine loops in the background while ultrasound imaging is ongoing is that a delay between when a user requests to review the results of the measurement and when the results are presented to the user may be reduced. Another technical effect is that more complex algorithms demanding higher processing resources may be applied without extending the duration of the patient exam. A still further technical effect is that the background measurement may be performed with processing resources that are available during image acquisition/generation (and that might otherwise go unused), which may improve the efficiency of the computing device executing the background measurement by reducing the total duration of time of a patient exam, and hence a total duration of time that processing resources are utilized.

The disclosure also provides support for a method, comprising: acquiring a first ultrasound image and a second ultrasound image in accordance with a patient exam workflow, wherein the patient exam workflow calls for one or more measurements including a first measurement to be obtained on at least the first ultrasound image, automatically assessing whether the first ultrasound image is suitable for obtaining the first measurement during a time period where the second ultrasound image is being acquired, and if the first ultrasound image is automatically assessed as being unsuitable for obtaining the first measurement, automatically prompting a user, while the second ultrasound image is still being acquired, to reacquire the first ultrasound image. In a first example of the method, the method further comprises: if the first ultrasound image is automatically assessed as being suitable for obtaining the first measurement, automatically starting the obtaining of the first measurement while the second ultrasound image is being acquired. In a second example of the method, optionally including the first example, the first measurement is obtained while the second ultrasound image is being acquired and while one or more additional ultrasound images are acquired, after the second ultrasound image is acquired, and further comprising, responsive to obtaining the first measurement, outputting a notification to the user indicating that the first measurement is available for review. In a third example of the method, optionally including one or both of the first and second examples, the method further comprises: determining that the first ultrasound image is suitable or unsuitable for obtaining the first measurement based on output from an anatomy view model, and wherein acquiring the first ultrasound image includes receiving an input from the user to store or freeze the first ultrasound image. In a fourth example of the method, optionally including one or more or each of the first through third examples, the second ultrasound image is acquired immediately following acquisition of the first ultrasound image without any intervening images being acquired. In a fifth example of the method, optionally including one or more or each of the first through fourth examples, automatically assessing whether the first ultrasound image is suitable for obtaining the first measurement comprises performing one or more steps specified to obtain the first measurement and performing a plurality of checks while performing the one or more steps. In some examples, all steps for obtaining the first measurement may be performed and the plurality of checks may be carried while the steps are being performed. In a sixth example of the method, optionally including one or more or each of the first through fifth examples, performing the plurality of checks comprises checking one or more meta parameters that were used during acquisition of the first ultrasound image. In a seventh example of the method, optionally including one or more or each of the first through sixth examples, performing the plurality of checks comprises using an anatomy view model to confirm that the first ultrasound image includes a correct anatomy view.

The disclosure also provides support for a method executable by a computing device in communication with an ultrasound probe, comprising: acquiring, with the ultrasound probe and the computing device, a plurality of ultrasound images of a patient in accordance with a patient exam workflow that includes a background measurement to be performed with one or more selected ultrasound images of the plurality of ultrasound images, determining, with the computing device, that the one or more selected ultrasound images have been saved as part of the patient exam workflow, and in response, automatically executing, with the computing device, the background measurement on the one or more selected ultrasound images while remaining ultrasound images of the plurality of ultrasound images are still being acquired, and outputting, with the computing device, a notification related to the background measurement for display on a display device. In a first example of the method, outputting the notification comprises determining, with the computing device, that the background measurement was executed with confidence, and in response, outputting the notification indicating that the background measurement is available for review. In a second example of the method, optionally including the first example, the method further comprises: outputting a result of the background measurement for display on the display device in response to a user input associated with the notification. In a third example of the method, optionally including one or both of the first and second examples, outputting the notification comprises determining, with the computing device, that the background measurement was not executed with confidence, and in response, outputting the notification indicating that the background measurement could not be performed and/or that one or more of the one or more selected ultrasound images should be reacquired. In a fourth example of the method, optionally including one or more or each of the first through third examples, determining that the one or more selected ultrasound images have been saved as part of the patient exam workflow comprises entering each ultrasound image of the plurality of ultrasound images, as each ultrasound image is saved, into an anatomy view model configured to output an anatomy view of each ultrasound image, and determining that the one or more selected ultrasound images have been saved as part of the patient exam workflow in response to output from the anatomy view model indicating that each of the one or more selected ultrasound images includes a respective anatomy view for executing the background measurement. In a fifth example of the method, optionally including one or more or each of the first through fourth examples, the method further comprises: upon acquiring each image of the plurality of ultrasound images, performing one or more additional measurements on one or more of the plurality of ultrasound images in response to a user request to perform the one or more additional measurements. In a sixth example of the method, optionally including one or more or each of the first through fifth examples, automatically executing, with the computing device, the background measurement on the one or more selected ultrasound images while remaining ultrasound images of the plurality of ultrasound images are still being acquired comprises: assigning a first, lower processing priority to the executing of the background measurement, assigning a second, higher processing priority to processing of ultrasound data to acquire the remaining ultrasound images, and allocating processing resources of the computing device according to each assigned priority. In a seventh example of the method, optionally including one or more or each of the first through sixth examples, the patient exam workflow comprises an echocardiogram, wherein the background measurement comprises a myocardial wall strain measurement of a heart of the patient, and wherein the one or more selected ultrasound images comprise a first image including a 4-chamber view of the heart, a second image including a 2-chamber view of the heart, and a third image including a long axis view of the heart.

The disclosure also provides support for a system, comprising: a computing device including instructions stored in memory executable by one or more processors to: receive ultrasound data from an ultrasound probe and process the ultrasound data to generate ultrasound images, as each ultrasound image is generated, display that ultrasound image on a display device, responsive to user input, save one or more of the ultrasound images, responsive to determining that one or more selected ultrasound images have been saved, execute a background measurement with the one or more selected ultrasound images, the background measurement executed while a subset of the ultrasound data is being processed to generate one or more corresponding ultrasound images, and display a notification on the display device that the background measurement is available to view. In a first example of the system, executing the background measurement with the one or more selected ultrasound images while the subset of the ultrasound data is being processed to generate one or more corresponding ultrasound images comprises: assigning a first, lower processing priority to the executing of the background measurement, assigning a second, higher processing priority to processing of the subset of the ultrasound data, and allocating processing resources of the computing device according to each assigned priority. In a second example of the system, optionally including the first example, the processing of the subset of the ultrasound data comprises performing a scan conversion process on channel data received from the ultrasound probe to form the one or more corresponding ultrasound images, and wherein the one or more corresponding ultrasound images are displayed on the display device as the one or more corresponding ultrasound images are generated. In a third example of the system, optionally including one or both of the first and second examples, the instructions are further executable to display a result of the background measurement on the display device in response to a second user input associated with the notification, and wherein one or more selected ultrasound images comprise a series of ultrasound images generated from ultrasound data acquired across an entire cardiac cycle of a patient.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements.

Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
   acquiring a first ultrasound image and a second ultrasound image in accordance with a patient exam workflow, wherein the patient exam workflow calls for one or more measurements including a first measurement to be obtained on at least the first ultrasound image;
   automatically assessing whether the first ultrasound image is suitable for obtaining the first measurement during a time period where the second ultrasound image is being acquired;
   determining that the first ultrasound image is unsuitable for obtaining the first measurement, and in response, automatically prompting a user, while the second ultrasound image is still being acquired, to reacquire the first ultrasound image;
   reacquiring the first ultrasound image;
   automatically assessing whether the reacquired first ultrasound image is suitable for obtaining the first measurement during a time period where a third ultrasound image is being acquired, the third ultrasound image acquired in accordance with the patient exam workflow; and
   determining that the reacquired first image is suitable for obtaining the first measurement, and in response, automatically starting the obtaining of the first measurement while the third ultrasound image is being acquired.

2. The method of claim 1, wherein automatically starting the obtaining of the first measurement while the third ultrasound image is being acquired comprises:
   assigning a first, lower processing priority to the obtaining of the first measurement;
   assigning a second, higher processing priority to processing of ultrasound data to acquire the third ultrasound image and one or more additional ultrasound images; and
   allocating processing resources of the computing device according to each assigned priority.

3. The method of claim 1, wherein the first measurement is obtained while the third ultrasound image is being acquired and displayed and while one or more additional ultrasound images are acquired and displayed, after the third ultrasound image is acquired, and further comprising, responsive to obtaining the first measurement, outputting a notification to the user indicating that the first measurement is available for review.

4. The method of claim 1, wherein automatically assessing whether the first ultrasound image is suitable for obtaining the first measurement comprises automatically assessing whether the first ultrasound image is suitable for obtaining the first measurement based on output from an anatomy view model, and wherein acquiring the first ultrasound image includes receiving an input from the user to store or freeze the first ultrasound image.

5. The method of claim 1, wherein the second ultrasound image is acquired immediately following acquisition of the first ultrasound image without any intervening images being acquired.

6. The method of claim 1, wherein automatically assessing whether the first ultrasound image is suitable for obtaining the first measurement comprises performing one or more steps specified to obtain the first measurement and performing a plurality of checks while performing the one or more steps.

7. The method of claim 6, wherein performing the plurality of checks comprises checking one or more meta parameters that were used during acquisition of the first ultrasound image.

8. The method of claim 7, wherein performing the plurality of checks comprises using an anatomy view model to confirm that the first ultrasound image includes a correct anatomy view.

* * * * *